(12) United States Patent
Igaue (10) Patent No.: US 10,980,665 B2
(45) Date of Patent: Apr. 20, 2021

(54) HEAT GENERATOR

(71) Applicant: Kobayashi Pharmaceutical Co., Ltd., Osaka (JP)

(72) Inventor: Tsuyoshi Igaue, Ibaraki (JP)

(73) Assignee: KOBAYASHI PHARMACEUTICAL CO., LTD., Osaka (JP)

( * ) Notice: Subject to any disclaimer, the term of this patent is extended or adjusted under 35 U.S.C. 154(b) by 133 days.

(21) Appl. No.: 16/098,065

(22) PCT Filed: May 2, 2016

(86) PCT No.: PCT/JP2016/063608
§ 371 (c)(1),
(2) Date: Jan. 31, 2019

(87) PCT Pub. No.: WO2017/191680
PCT Pub. Date: Nov. 9, 2017

(65) Prior Publication Data
US 2020/0046550 A1 Feb. 13, 2020

(51) Int. Cl.
*A61F 7/00* (2006.01)
*A61F 7/03* (2006.01)
(Continued)

(52) U.S. Cl.
CPC .................. *A61F 7/03* (2013.01); *A61K 9/70* (2013.01); *A61F 2007/0098* (2013.01);
(Continued)

(58) Field of Classification Search
CPC .... A61F 7/03; A61F 7/034; A61F 2007/0098; A61F 2007/0226; A61F 2007/038;
(Continued)

(56) References Cited

U.S. PATENT DOCUMENTS

2008/0202490 A1 8/2008 Dodo
2008/0257333 A1* 10/2008 Dodo ....................... C09K 5/18
126/263.09
(Continued)

FOREIGN PATENT DOCUMENTS

EP 1 782 770 A1 5/2007
EP 3 251 637 A1 12/2017
(Continued)

OTHER PUBLICATIONS

European Search Report, re Application No. 16901067.5, dated Nov. 29, 2019.
(Continued)

*Primary Examiner* — Alfred Basichas
(74) *Attorney, Agent, or Firm* — Knobbe, Martens, Olson & Bear, LLP (57) ABSTRACT

The purpose of the present invention is to provide a heat generator that contains a volatile component and in which the volatile component is stably maintained during storage, the volatile component is prevented from adhering to a heat-generating section, and it is possible to achieve an excellent warming effect during use. This heat generator comprises a heat-generating section (1), an accommodation body (2) for accommodating the heat-generating section (1), an adhesive layer (3) provided to an attachment surface side of the accommodation body (2), and a release sheet (4) provided to the attachment surface side of the adhesive layer (3). As a result of including a volatile component in the adhesive layer (3) and respectively providing gas barrier layers (211), (41) to a first packaging material (21) constituting the attachment surface side of the accommodation body (2) and to the release sheet (4), it is possible to stably maintain the volatile component within the adhesive layer (3) during storage. It is thereby possible to prevent the volatile component from adhering to the heat-generating
(Continued)

section (1) during storage and to achieve an excellent warming effect during use.

8 Claims, 3 Drawing Sheets (51) Int. Cl.
    *A61K 9/70*     (2006.01)
    *F24V 30/00*     (2018.01)
    *A61F 7/02*     (2006.01)

(52) U.S. Cl.
    CPC . *A61F 2007/0226* (2013.01); *A61F 2007/038* (2013.01); *F24V 30/00* (2018.05)

(58) Field of Classification Search
    CPC ...... A61F 2007/0257; A61F 2007/0207; A61F 2007/022; A61F 2007/0261; A61K 9/70; F24V 30/00
    See application file for complete search history.

(56) References Cited

U.S. PATENT DOCUMENTS

2011/0190714 A1     8/2011     Oda et al.
2015/0211766 A1     7/2015     Yasuda et al.
2017/0258632 A1     9/2017     Inoue et al.

FOREIGN PATENT DOCUMENTS

| EP | 3 348 242 A1 | 7/2018 |
|---|---|---|
| JP | 2002-360624 A | 12/2002 |
| JP | 2005-170865 A | 6/2005 |
| JP | 2009-248453 A | 10/2009 |
| JP | 2009-274768 A | 11/2009 |
| JP | 2011-160885 | 8/2011 |
| JP | 2013-042963 A | 3/2013 |
| JP | 2014-030486 A | 2/2014 |
| JP | 2014-205072 A | 10/2014 |
| WO | WO 2006/006650 A1 | 1/2006 |
| WO | WO 2016/017733 A1 | 2/2016 |

OTHER PUBLICATIONS

International Search Report for International Application No. PCT/JP2016/063608 dated Jun. 21, 2016 (in 2 pages).
Chinese Office Action, in CN Patent Application No. 201680085343.X, dated Jun. 18, 2020.

\* cited by examiner

HEAT GENERATOR

TECHNICAL FIELD

The present invention relates to a heat generator that is used by being attached to an adherend such as a skin or clothing and that contains a volatile component. More specifically, the present invention relates to a heat generator including a pressure-sensitive adhesive layer containing a volatile component, where the volatile component is stably maintained in the pressure-sensitive adhesive layer during storage, so that the functions provided by the volatile component and the warming functions are excellent during use.

BACKGROUND ART

A heat generator using a heat-generating composition that generates heat by being brought into contact with air is widely used not only as a warming tool for prevention of coldness or the like but also as a curing tool or the like for promotion of good blood circulation, alleviation of pain, or the like. Also, in recent years, by receiving enhanced demand for improvement in the functionality of heat generators, development of a heat generator imparted with various functionalities is put to trial.

Conventionally, there is developed a heat generator that can impart scent or sensation of coolness by incorporation of a volatile component. For example, Patent Document 1 reports a heat generator in which a heat-generating section including an oxidizable metal, a reaction promoter, an electrolyte, and water is accommodated in an accommodation body, where the heat-generating section contains a cold sensation imparting agent that imparts coolness to the skin and a solvent that dissolves the cold sensation imparting agent. However, a heat generator in which the cold sensation imparting agent is directly blended in the heat-generating section such as disclosed in Patent Document 1 has disadvantages such that the cold sensation imparting agent is adhered to an oxidation promoter (activated carbon or the like) that is contained in the heat-generating section, whereby the sensation of coolness given by the cold sensation imparting agent may decrease, and further, the warming function exhibited by the heat-generating section may decrease or become non-uniform.

In the meantime, there is also a report on a heat generator in which a volatile component is incorporated into a constituent member other than a heat-generating section. For example, Patent Document 2 discloses that a heat generator provided with a heat-generating section containing an oxidizable metal and activated carbon, and a bag body at least a part of which has gas permeability and which accommodates the heat-generating section, where a scent-imparting sheet in which a perfume composition containing a monoterpenoid having a cyclic ether structure and a monoterpenoid having a cyclic ketone structure is incorporated at a specific ratio is disposed between the heat-generating body and the bag body, provides good rise in the scent during use, and degeneration of scent during storage hardly occurs. Also, Patent Document 3 discloses that a heat generator having a heat-generating section containing an oxidizable metal and activated carbon, and a bag body that is constituted with a sheet at least a part of which has gas permeability and at least a part of which has a weight of 20 to 90 g/m$^2$ and that accommodates the heat-generating section, where a scent-imparting sheet, in which a perfume composition containing 0.2 to 0.7 mass % of damascenone is incorporated, is disposed between the heat-generating body and the bag body, exhibits a good scent, which is of the time immediately after production, during use as well. However, since a heat generator is stored generally in a state of being accommodated in a tight sealing bag, even the cases of incorporating a volatile component into a constituent member other than a heat-generating section such as disclosed in Patent Documents 2 and 3 have disadvantages such that, by migration and adsorption of the volatile component into the heat-generating section during storage, the function of the volatile component itself may decrease, and further, the warming function provided by the heat-generating section may decrease or become non-uniform.

PRIOR ART DOCUMENTS

Patent Documents

Patent Document 1: Japanese Patent Laid-open Publication No. 2014-205072

Patent Document 2: Japanese Patent Laid-open Publication No. 2011-160885

Patent Document 3: Japanese Patent Laid-open Publication No. 2013-42963

SUMMARY OF THE INVENTION

Problems to be Solved by the Invention

In a heat generator in which a volatile component is incorporated into a constituent member other than a heat-generating section such as disclosed in Patent Documents 2 and 3, migration of the volatile component into the heat-generating section during storage seems to be caused by direct migration of the volatile component into the heat-generating body from the member containing the volatile component or by permeation of the volatile component into the heat-generating section from a gas-permeable site of the bag body that accommodates the heat-generating section through volatilization of the volatile component in the tight sealing bag.

Accordingly, an object of the present invention is to provide a heat generator that contains a volatile component and in which the volatile component is stably maintained during storage, the volatile component is prevented from adhering to the heat-generating section, and it is possible to achieve an excellent warming effect during use.

Means for Solving the Problems

The present inventor has made eager studies in order to solve the aforementioned problems and has found out that a heat generator having a heat-generating section, an accommodation body for accommodating the heat-generating section, a pressure-sensitive adhesive layer provided to an attachment surface side of the accommodation body, and a release sheet provided to the attachment surface side of the pressure-sensitive adhesive layer, in which a volatile component is incorporated into the pressure-sensitive adhesive layer and in which gas barrier layers are respectively provided to a first packaging material constituting the attachment surface side of the accommodation body and to the release sheet, makes it possible to stably maintain the volatile component within the pressure-sensitive adhesive layer during storage and, as a result, makes it possible to prevent the volatile component from adhering to the heat-generating section during storage and to achieve an excellent warming effect during use. The present invention has been completed by repetitively making further studies based on such knowledge.

That is, the present invention provides inventions having modes listed in the following.

Item 1: A heat generator that is used by being attached to an adherend, the heat generator comprising:
a heat-generating section for generating heat that is transmitted to the adherend;
an accommodation body for accommodating the heat-generating section, the accommodation body having an attachment surface that is attached to the adherend;
a pressure-sensitive adhesive layer provided to an attachment surface side of the accommodation body; and
a release sheet provided to an attachment surface side of the pressure-sensitive adhesive layer and being releasable from the pressure-sensitive adhesive layer, wherein
the pressure-sensitive adhesive layer contains a volatile component,
a first packaging material disposed on the attachment surface side of the accommodation body includes a first gas barrier layer, and
the release sheet includes a second gas barrier layer.

Item 2: The heat generator according to Item 1, wherein the first packaging material has an oxygen permeability of 1.5 cc/m$^2$·day·atm or less.

Item 3: The heat generator according to Item 1 or 2, wherein the release sheet has an oxygen permeability of 1.5 cc/m$^2$·day·atm or less.

Item 4: The heat generator according to any one of Items 1 to 3, wherein the first packaging material has a water vapor permeability of 1.5 g/m$^2$·day·atm or less.

Item 5: The heat generator according to any one of Items 1 to 4, wherein the release sheet has a water vapor permeability of 1.5 g/m$^2$·day·atm or less.

Item 6: The heat generator according to any one of Items 1 to 5, wherein
the accommodation body is composed of the first packaging material and a second packaging material that is disposed on a surface opposite to the attachment surface,
the accommodation body includes a peripheral bonding section where peripheral parts of the first packaging material and the second packaging material are bonded, and an accommodation section that forms a space for accommodating the heat-generating section, and
the pressure-sensitive adhesive layer is provided at least in a region where the peripheral bonding section of the first packaging material is formed.

Item 7: The heat generator according to any one of Items 1 to 6, wherein the volatile component is at least one kind selected from the group consisting of menthol, camphor, thymol, spilanthol, mint oil, peppermint oil, methyl salicylate, capsaicin, vanillyl nonylic acid amide, sage, caffeine, tocopherol nicotinate, benzyl nicotinate, vanillyl butyl ether, vanillyl ethyl ether, gingerol, vanillyl propyl ether, vanillyl pentyl ether, vanillyl hexyl ether, vanillyl butyl ether acetate, hot pepper extract, and ginger extract.

Item 8: The heat generator according to any one of Items 1 to 7, wherein the release sheet does not have a penetrating section that penetrates in a thickness direction.

Advantages of the Invention

According to the heat generator of the present invention, it is possible to stably maintain the volatile component within the pressure-sensitive adhesive layer and to prevent the volatile component from adhering to the heat-generating section during storage, so that the functions and effects provided by the volatile component can be effectively enjoyed during use. Also, in the heat generator of the present invention, the heat generation characteristics of the heat-generating section are stably maintained by preventing the volatile component from adhering to the heat-generating section during storage, so that the heat generation temperature can be prevented from decreasing or becoming non-uniform during use, and an excellent warming effect can also be achieved during use.

EMBODIMENTS OF THE INVENTION

Figure 1:
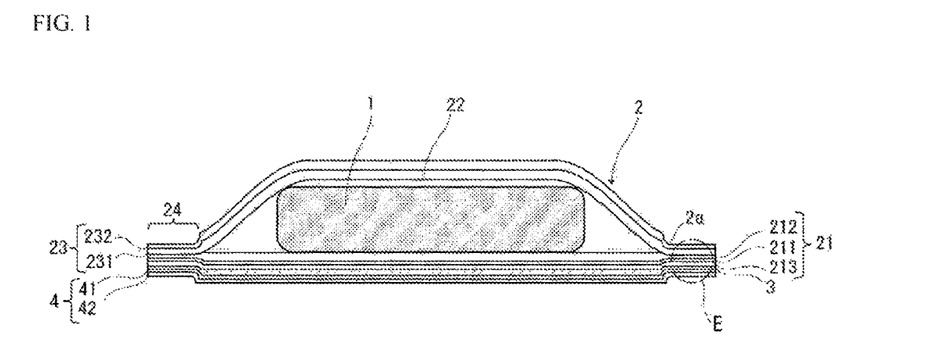
FIG. 1 is a schematic view of a cross-sectional structure of a preferable embodiment of the heat generator of the present invention.
Figure 2:
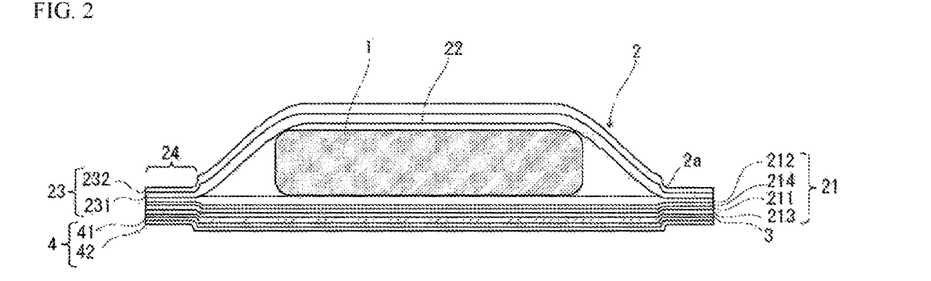
FIG. 2 is a schematic view of a cross-sectional structure of a preferable embodiment of the heat generator of the present invention.

The heat generator of the present invention is a heat generator that is used by being attached to an adherend and includes a heat-generating section 1 for generating heat that is transmitted to the adherend, an accommodation body 2 for accommodating the heat-generating section 1, the accommodation body 2 having an attachment surface that is attached to the adherend, a pressure-sensitive adhesive layer 3 provided to an attachment surface side of the accommodation body 2, and a release sheet 4 provided to an attachment surface side of the pressure-sensitive adhesive layer 3 and being releasable from the pressure-sensitive adhesive layer 3, characterized in that the pressure-sensitive adhesive layer 3 contains a volatile component; a first packaging material 21 disposed on the attachment surface side of the accommodation body 2 includes a first gas barrier layer 211; and the release sheet 4 includes a second gas barrier layer 41. Here, in the present invention, a gas barrier layer refers to a layer formed of a material that can suppress permeation of a volatile component. Hereafter, the heat generator of the present invention will be described in detail.

<Heat-Generating Section 1>

The heat generator of the present invention includes a heat-generating section 1 for generating heat that is transmitted to an adherend. The heat-generating section 1 performs a function of generating heat and imparting a sensation of hotness.

The heat generation mechanism of the heat-generating section 1 is not particularly limited as long as the heat-generating section 1 can generate heat and can transmit the heat to the adherend. Examples of the heat-generating section include a heat-generating composition that generates heat by being brought into contact with oxygen; an energization heat generating body that generates heat by being energized; a heat generating body that generates heat by receiving radiation of a microwave; and a heat generating body that generates heat by using a liquid, semisolid, or solid heat-storing material. Among these, a heat-generating composition that generates heat by being brought into contact with oxygen is strongly liable to invite decrease or weakening of the warming function by mingling of a volatile component or to invite non-uniform heat generation characteristics that are exhibited; however, in the heat generator of the present invention, such permeation of the volatile component into the heat-generating section 1 is effectively prevented. In view of such effects of the present invention, a heat-generating composition that generates heat by being brought into contact with oxygen is suitable as the heat-generating section 1. Also, a heat-generating composition that generates heat by being brought into contact with oxygen can be disposed of after being used and is hence suitable in view of safety, heat-generation efficiency, convenience, and the like as well.

The components of the heat-generating composition that generates heat by being brought into contact with oxygen are not particularly limited and may be those that are conventionally used in a disposable pocket warmer or the like. One suitable example of the heat-generating composition that generates heat by being brought into contact with oxygen may be a composition containing an oxidizable metal, an oxidation promoter, and water.

In the heat-generating composition, the oxidizable metal performs a function of being oxidized by being brought into contact with oxygen to become a heat generation source with oxidation heat. The type of the oxidizable metal is not particularly limited as long as heat can be generated by oxidation. Examples of the oxidizable metal include metals such as iron (reduced iron, cast iron, atomized iron, electrolytic iron), aluminum, zinc, manganese, magnesium, and calcium. These oxidizable metals may be used either alone as one kind or as a combination of two or more kinds.

Also, the shape of the oxidizable metal is not particularly limited; however, in view of the heat generation efficiency, the shape of the oxidizable metal is preferably powdery, granular, or fibrous, and more particularly is powdery.

Among these oxidizable metals, iron powder is preferable in view of safety, facility in handling, and the like.

When the oxidizable metal is powdery, the particle size thereof is not particularly limited and may be, for example, 0.01 to 1000 μu, preferably 0.1 to 500 μm, more preferably 0.5 to 300 μm, and still more preferably 30 to 250 μm. Here, the particle size of the powdery oxidizable metal is a value that is determined in accordance with "Dry sieving test" defined in JIS8815-1994 "Test sieving—General requirements".

The content of the oxidizable metal in the heat-generating composition is suitably set in accordance with the heat generation characteristics that are to be imparted, and may be, for example, 20 to 80 wt %, preferably 25 to 70 wt %, and more preferably 30 to 60 wt %.

Also, in the heat-generating composition, the oxidation promoter performs a function of retaining oxygen and supplying oxygen to the oxidizable metal. The type of the oxidation promoter is not particularly limited as long as the oxidation promoter can retain oxygen and supply oxygen to the oxidizable metal. Examples of the oxidation promoter include carbon materials such as activated carbon, carbon black, acetylene black, bamboo carbon, charcoal, coffee residue carbon, graphite, coal, coconut shell carbon, bituminous coal, peat, and lignite. These oxidation promoters may be used either alone as one kind or as a combination of two or more kinds.

Among these oxidation promoters, activated carbon, carbon black, bamboo carbon, charcoal, and coffee residue carbon are preferable, and activated carbon is more preferable.

Also, the shape of the oxidation promoter is not particularly limited; however, in view of the heat generation efficiency, the shape of the oxidation promoter is preferably powdery, granular, or fibrous, and more particularly is powdery.

When the oxidation promoter is powdery, the particle size thereof is not particularly limited and may be, for example, 0.001 to 1000 μm, preferably 0.005 to 500 pun, and more preferably 0.01 to 200 μm. Here, the particle size of the powdery oxidation promoter is a value that is determined in accordance with "Dry sieving test" defined in JIS8815-1994 "Test sieving—General requirements".

The content of the oxidation promoter in the heat-generating composition is suitably set in accordance with the heat generation characteristics that are to be imparted and the like, and may be, for example, 1 to 30 wt %, preferably 3 to 25 wt %, and more preferably 5 to 23 wt %.

Also, in the heat-generating composition, the ratio of the oxidation promoter to the oxidizable metal is suitably set in accordance with the heat generation characteristics that are to be imparted, and may be, for example, such that the oxidation promoter is contained at 2 to 60 parts by weight, preferably 5 to 50 parts by weight, and more preferably 10 to 40 parts by weight, relative to 100 parts by weight of the oxidizable metal.

Further, in the heat-generating composition, water performs a function of oxidizing the oxidizable metal together with oxygen. Water to be used may be any of distilled water, ion exchange water, pure water, ultrapure water, tap water, industrial water, and the like.

The content of water in the heat-generating composition is suitably set in accordance with the heat generation characteristics that are to be imparted, and may be, for example, 5 to 50 wt %, preferably 10 to 40 wt %, and more preferably 15 to 35 wt %.

In addition to the aforementioned components, the heat-generating composition may contain water-soluble salts in accordance with the needs. When water-soluble salts are contained, oxidation of the oxidizable metal can be promoted.

The type of the water-soluble salt is not particularly limited, and examples thereof include sulfates, hydrogen-carbonates, chlorides, and hydroxides of alkali metals (sodium, potassium, and others), alkaline earth metals (calcium, magnesium, and others), and heavy metals (iron, copper, aluminum, zinc, nickel, silver, barium, and others). Among these water-soluble salts, chlorides such as sodium chloride, potassium chloride, calcium chloride, magnesium chloride, and iron chloride (ferrous chloride, ferric chloride) are preferable, and sodium chloride is more preferable, in view of electric conductivity, chemical stability, and the like. These water-soluble salts may be used either alone as one kind or as a combination of two or more kinds.

When a water-soluble salt is blended into the heat-generating composition, the content of the water-soluble salt is suitably set in accordance with the heat generation characteristics that are to be imparted, and may be, for example, 0.1 to 10 wt %, preferably 0.5 to 7 wt %, and more preferably 1 to 5 wt %.

Further, the heat-generating composition may contain a water retention agent in accordance with the needs. The water retention agent performs a function of retaining water and supplying water to the oxidation reaction field.

The type of the water retention agent is not particularly limited, and examples thereof include inorganic porous materials such as vermiculite (expanded vermiculite), pearlite, calcium silicate, magnesium silicate, kaolin, talc, smectite, mica, bentonite, calcium carbonate, silica gel, alumina, zeolite, silicon dioxide, and diatomaceous earth; organic materials such as pulp, wood powder (sawdust), cotton, starches, and celluloses: and water-absorbing resins such as polyacrylate resin, polysulfonate resin, maleic anhydride resin, polyacrylamide resin, polyvinyl alcohol resin, polyethylene oxide resin, polyaspartate resin, polyglutamate resin, and polyalginate resin. These water retention agents may be used either alone as one kind or as a combination of two or more kinds.

Among these water retention agents, vermiculite, polyacrylate resin, wood powder, and pulp are preferable; and vermiculite and polyacrylate resin are more preferable. Also, when an inorganic porous material is used as the water retention agent, an air flow passageway can also be ensured in the heat-generating composition.

The particle size of the water retention agent is not particularly limited and may be, for example, 0.1 to 3000 μm, preferably 0.5 to 1000 μm, and more preferably 1 to 1000 μm. Here, the particle size of the water retention agent is a value that is determined in accordance with "Dry sieving test" defined in JIS8815-1994 "Test sieving—General requirements".

When a water retention agent is blended into the heat-generating composition, the content of the water retention agent is suitably set in accordance with the heat generation characteristics that are to be imparted, and may be, for example, 1 to 20 wt %, preferably 3 to 15 wt %, and more preferably 5 to 10 wt %.

The heat-generating composition may further contain other additives such as a metal ion blocking agent, a perfume, a thickening agent, an excipient, a surfactant, and a hydrogen generation suppresser in accordance with the needs.

The heat-generating composition can be prepared by blending predetermined amounts of the aforementioned components. The preparation of the heat-generating composition may be carried out in the presence of oxygen; however, the heat-generating composition is preferably prepared under reduced pressure or in an inert gas atmosphere.

The heat-generating section 1 is set so that heat is generated to achieve a suitable temperature when the heat generator of the present invention is attached to the adherend. The maximum attained temperature of the heat generator of the present invention may be suitably set in accordance with the type and site of the adherend serving as an object of application, the sensation of hotness and warming function to be imparted, and the like, and may be, for example, about 32 to 85° C., preferably about 34 to 70° C. The maximum attained temperature is a value determined in accordance with the method defined in JIS S4100:2007.

<Accommodation Body 2>

The heat generator of the present invention is provided with an accommodation body 2 that accommodates the heat-generating section 1. The accommodation body 2 has an accommodation section 22 for accommodating the heat-generating section 1.

In the accommodation body 2, a first packaging material 21 disposed on the attachment surface side that is attached to the adherend includes at least a first gas barrier layer 211. The first gas barrier layer 211 performs a function of preventing the volatile component contained in the pressure-sensitive adhesive layer 3 from directly migrating into the inside of the accommodation section 22.

The oxygen permeability of the first packaging material 21 is not particularly limited as long as the first packaging material 21 can prevent permeation of the volatile component; however, in view of more effectively preventing direct migration of the volatile component into the inside of the accommodation section 22, the oxygen permeability of the first packaging material 21 may be, for example, 1.5 $cc/m^2 \cdot day \cdot atm$ or less, preferably 0 to 1 $cc/m^2 \cdot day \cdot atm$, more preferably 0 to 0.5 $cc/m^2 \cdot day \cdot atm$, and still more preferably 0 to 0.1 $cc/m^2 \cdot day \cdot atm$. In the present specification, the "oxygen permeability" is a value determined under conditions with a temperature of 20° C. and a humidity of 90% RH in accordance with the differential pressure method defined in JIS K 7126-1:2006.

Also, the water vapor permeability of the first packaging material 21 is not particularly limited as long as the first packaging material 21 can prevent permeation of the volatile component; however, in view of more effectively preventing direct migration of the volatile component into the inside of the accommodation section 22, the water vapor permeability of the first packaging material 21 may be, for example, 1.5 $g/m^2 \cdot day$ or less, preferably 0 to 1 $g/m^2 \cdot day$, more preferably 0 to 0.5 $g/m^2 \cdot day$, and still more preferably 0 to 0.1 $g/m^2 \cdot day$. In the present specification, the "water vapor permeability" is a value determined under conditions with a temperature of 40° C. and a humidity of 90% RH in accordance with the cup method defined in JIS Z0208:1976.

The material constituting the first gas barrier layer 211 is not particularly limited and may be, for example, a metal foil membrane, a vapor deposition film, a thermoplastic resin layer capable of shutting off the permeation of volatile components (which may hereafter be denoted as "barrier resin layer"), or the like.

The metal foil constituting the metal foil membrane used as the first gas barrier layer 211 may be, for example, an aluminum foil, a stainless steel foil, or the like. Among these metal foils, an aluminum foil is preferable.

The thickness of the metal foil membrane is not particularly limited and may be, for example, 5 to 50 μm, preferably 5 to 15 μm.

The metal foil membrane can be laminated onto a material that forms an adjacent layer by a known lamination method such as dry lamination, extrusion lamination, or heat lamination.

The material that constitutes a vapor deposition film used as the first gas barrier layer 211 is not particularly limited as long as the material can shut off the permeation of volatile components, and examples of the material include metals such as aluminum, chromium, zinc, gold, silver, platinum, and nickel; inorganic oxides such as silica, titanium oxide, aluminum oxide, and zirconium oxide; and inorganic fluorides such as magnesium fluoride.

The thickness of the vapor deposition film is not particularly limited as long as the thickness is within a range such that the permeation of volatile components can be prevented, and the thickness may be, for example, 50 to 5000 Å, preferably 100 to 1000 Å.

The vapor deposition film can be formed by vapor deposition of the aforementioned material onto a material that forms an adjacent layer by a known vapor deposition method such as the physical vapor deposition method or the chemical vapor deposition method.

The resin constituting the barrier resin layer used as the first gas barrier layer 211 is not particularly limited as long as the resin can shut off the permeation of volatile components, and the resin may be, for example, polyvinylidene chloride.

The barrier resin layer can be formed by forming a coating film on a material that forms an adjacent layer by a known resin coating method.

The thickness of the barrier resin layer is not particularly limited as long as the thickness is within a range such that the permeation of volatile components can be prevented, and the thickness may be, for example, 0.5 to 30 µm, preferably 0.8 to 10 µm, and more preferably 1 to 2 µm.

In the first packaging material 21, the first gas barrier layer 211 may be a single layer made of one constituent material or a multiple layer made of two or more of the same or different materials. Among the materials constituting the first gas barrier layer 211, the first gas barrier layer 211 is preferably made of a metal foil membrane or a vapor deposition film, more preferably a metal foil membrane, and still more preferably an aluminum foil membrane, in view of more effectively preventing direct migration of the volatile component into the inside of the accommodation section 22 and stably maintaining the volatile component within the pressure-sensitive adhesive layer 3 during storage. Also, when a metal foil membrane or a vapor deposition film is used as the first gas barrier layer 211, the heat conductivity from the heat-generating section 1 to the adherend is improved, so that hotness can be perceived early from the start of use, and further the sensation of hotness can be improved by radiation heat that is emitted from the metal foil membrane or vapor deposition film.

In the first packaging material 21, it is preferable that a welded resin layer 212 formed of a thermoplastic resin excellent in heat weldability is laminated onto the accommodation section 22 side of the first gas barrier layer 211. By providing the welded resin layer 212 in such a manner, peripheral parts of the first packaging material 21 and the second packaging material 23 that is disposed opposite to the attachment surface side can be easily bonded, and the accommodation section 2 can be formed in a convenient and simple manner. The thermoplastic resin constituting the welded resin layer 212 may be specifically, for example, a polyolefin such as polyethylene or polypropylene.

The thickness of the welded resin layer 212 is not particularly limited and may be, for example, 1 to 200 µm, preferably 30 to 100 µm.

Further, in the first packaging material 21, it is preferable that a fiber substrate 213 is laminated onto the surface of the first gas barrier layer 211 that is in surface contact with the pressure-sensitive adhesive layer 3. By providing the fiber substrate 213 in this manner, the temperature of the attachment surface of the heat generator of the present invention onto the adherend can be adjusted, and also the sensation of use at the time of attaching the heat generator of the present invention onto a skin can be improved.

The fiber substrate 213 may be specifically, for example, a nonwoven cloth or woven cloth. In view of the sensation of use and the like, the fiber substrate 213 is preferably made of a nonwoven cloth. The material of the fiber substrate 213 is not particularly limited, and examples thereof include synthetic fibers such as polyethylene terephthalate, polybutylene terephthalate, nylon, polypropylene, polyethylene, vinylon, rayon, acryl, acetate, and polyvinyl chloride; natural fibers such as cotton, linen, silk, and paper; and mixed fibers of these. Among these materials, the fiber substrate 213 is preferably made of polyethylene terephthalate, nylon, or polypropylene, more preferably polyethylene terephthalate or nylon, in view of enhancing the sensation of use.

The weight per unit area of the fiber substrate 213 may be suitably set in accordance with the layer configuration of the first packaging material 21 and the like, and may be, for example, 10 to 100 g/m$^2$, preferably 15 to 70 g/m$^2$, and more preferably 20 to 50 g/m$^2$.

The fiber substrate 213 can be laminated onto a material that forms an adjacent layer by a known lamination method such as dry lamination, extrusion lamination, or heat lamination.

Further, besides the aforementioned layers, the first packaging material 21 may include a first resin layer 214 made of a resin layer other than the barrier resin layer and the welded resin layer 212 in accordance with the needs. In particular, the first resin layer is used as a substrate layer for supporting the vapor deposition film or the barrier resin layer when the vapor deposition film or the barrier resin layer is used as the first gas barrier layer 211.

When the first resin layer 214 is provided in the first packaging material 21, the first resin layer 214 may be disposed, for example, between the welded resin layer 212 and the first gas barrier layer 211 and/or between the first gas barrier layer 211 and the fiber substrate 213.

The resin constituting the first resin layer 214 is not particularly limited and may be, for example, a thermoplastic resin such as polyethylene terephthalate, polyacrylonitrile, or ethylene-vinyl alcohol copolymer. Among these resins, polyethylene terephthalate is a preferable example.

The thickness of the first resin layer 214 is not particularly limited and may be, for example, 1 to 100 µm, preferably 3 to 50 µm.

A preferable mode of the layer structure of the first packaging material 21 may be, for example, a lamination structure in which the welded resin layer 212, the first gas barrier layer 211 made of a metal foil membrane, and the fiber substrate 213 are laminated in this order; or a lamination structure in which the welded resin layer 212, the first resin layer 214, the first gas barrier layer 211 made of a vapor deposition film, and the fiber substrate 213 are laminated in this order, in a direction from the inside of the accommodation section 22 towards the pressure-sensitive adhesive layer 3 side.

The second packaging material 23 that is disposed opposite to the attachment surface side in the accommodation body 2 can be formed of a material similar to that of a skin attachment surfaced side packaging material of the accommodation body 2 in a conventional heat generator. When a heat-generating composition that generates heat by being brought into contact with oxygen is used as the heat-generating section 1, it is necessary that the second packaging material 23 is provided with gas permeability. However, when a material other than the heat-generating composition is used as the heat-generating section 1, the second packaging material 23 may be either gas-permeable or non-gas-permeable.

The second packaging material 23 having gas permeability can be formed, for example, with a gas-permeable resin layer 231, a fiber substrate 232, and the like.

The constituent resin of the gas-permeable resin layer 231 used for forming the second packaging material 23 having gas permeability is not particularly limited, and may be, for example, a thermoplastic resin. Specific examples of the thermoplastic resin include polyethylene, polypropylene, ethylene-vinyl acetate copolymer, polyethylene terephthalate, polyacrylonitrile, ethylene-vinyl alcohol copolymer, polyamide, polyurethane, polystyrene, polyvinyl alcohol, polyvinyl chloride, polyvinylidene chloride, and polycarbonate. Among these thermoplastic resins, polyethylene, polypropylene, and ethylene-vinyl acetate copolymer are preferable examples.

Also, the gas-permeable resin layer 231 may be specifically a resin film in which pores for ensuring gas permeability are provided. The shape, size, and number of the pores provided in the resin film may be suitably set in accordance with the gas permeability that is to be provided in the accommodation body 2.

The thickness of the gas-permeable resin layer 231 may be suitably set in accordance with the layer configuration of the second packaging material 23 and the like, and may be, for example, 15 to 150 µm, preferably 30 to 100 µm, and more preferably 50 to 80 µm.

The fiber substrate 232 used in the second packaging material 23 may be specifically, for example, a nonwoven cloth or woven cloth. In view of the sensation of use and the like, the fiber substrate 232 is preferably made of a nonwoven cloth. The material of the fiber substrate 232 is not particularly limited, and examples thereof include synthetic fibers such as polyethylene terephthalate, polybutylene terephthalate, nylon, polypropylene, polyethylene, vinylon, rayon, acryl, acetate, and polyvinyl chloride; natural fibers such as cotton, linen, silk, and paper; and mixed fibers of these. Among these materials, the fiber substrate 232 is preferably made of polyethylene terephthalate, nylon, or polypropylene, more preferably polyethylene terephthalate or nylon, in view of enhancing the sensation of use.

The weight per unit area of the fiber substrate 232 may be suitably set in accordance with the layer configuration of the second packaging material 23 and the like, and may be, for example, 1 to 100 g/m², preferably 5 to 70 g/m², and more preferably 10 to 50 g/m².

The layer structure of the second packaging material 23 having gas permeability may be specifically, for example, a single-layer structure made of the gas-permeable resin layer 231 or the fiber substrate 232; or a multiple-layer structure in which two or more of the same or different materials selected from the gas-permeable resin layer 231 and the fiber substrate 232 are combined. In view of improving the sensation of use, preventing leakage of the heat-generating composition, and the like, the layer structure of the second packaging material 23 is preferably a single-layer structure made of the gas-permeable resin layer 231 or a lamination structure in which the gas-permeable resin layer 231 and the fiber substrate 232 are laminated in this order in a direction from the inside of the accommodation body 2 towards the outside.

Lamination of the gas-permeable resin layer 231 and the fiber substrate 232 can be carried out by a known lamination method such as dry lamination, extrusion lamination, or heat lamination.

The accommodation body 2 is formed by bonding the first packaging material 21 and the second packaging material 23 at sites surrounding the region that is to become the accommodation section 22 for accommodating the heat-generating section 1. In other words, in the accommodation body 2, there are formed the accommodation section 22 that forms a space for accommodating the heat-generating section and the peripheral bonding section 24 where the peripheral parts of the first packaging material 21 and the second packaging material 23 are bonded. Also, when the peripheral parts of the first packaging material 21 and the second packaging material 23 are bonded in this manner, a step difference 2*a* (height difference) is formed at a boundary between the peripheral bonding section 24 and the accommodation section 22 (See FIG. 1).

A method for bonding the first packaging material 21 and the second packaging material 23 is not particularly limited. For example, a method of heat welding (heat sealing) by using the welded resin layer 212 included in the first packaging material 21, a method of bonding with use of an adhesive agent, or the like may be adopted.

When a heat-generating composition that generates heat by being brought into contact with oxygen is used as the heat-generating section 1, the amount of the heat-generating composition accommodated in the accommodation section 22 of the accommodation body 2 may be suitably set in accordance with the type and site of the adherend that is to be attached, the heat generation characteristics of the heat-generating composition, and the like, and may be, for example, such that the amount of the heat-generating composition is about 0.01 to 1.5 g, preferably about 0.05 to 1 g, and more preferably about 0.1 to 0.8 g, per 1 cm² of the area of the first packaging material 21 in the region that forms the accommodation section 22.

In the accommodation body 2 used in the present invention, the number of the accommodation sections 22 that accommodate the heat-generating section 1 is not particularly limited and may be either one or plural. The number of the accommodation sections 22 is suitably set in accordance with the type and site of the adherend that is to be attached or the like. Also, the size and shape of the accommodation section 22 is not particularly limited and is suitably set in accordance with the shape of the adherend that is to be attached or the like.

<Pressure-Sensitive Adhesive Layer 3>

In the heat generator of the present invention, a pressure-sensitive adhesive layer 3 containing a volatile component is provided to the attachment surface in the accommodation body 2. By providing such a pressure-sensitive adhesive layer 3, it is possible to attach the heat generator to a predetermined site of the adherend in a convenient and simple manner without separately using a fixing tool for fixing the heat generator onto the adherend. Also, since the volatile component is contained in the pressure-sensitive adhesive layer 3, it is possible to exhibit a function based on the volatile component together with the warming function during use.

The type of the volatile component contained in the pressure-sensitive adhesive layer 3 is not particularly limited, and may be, for example, a component having volatility and being capable of imparting fragrance, sensation of coolness, sensation of hotness, and the like. Specific examples of such a volatile component include cold sensation imparting agents such as menthol, camphor, thymol, spilanthol, mint oil, peppermint oil, and methyl salicylate; hot sensation imparting agents such as capsaicin, vanillyl nonylic acid amide, sage, caffeine, tocopherol nicotinate, benzyl nicotinate, vanillyl butyl ether, vanillyl ethyl ether, gingerol, vanillyl propyl ether, vanillyl pentyl ether, vanillyl hexyl ether, vanillyl butyl ether acetate, hot pepper extract (extract of hot pepper with water or water-containing ethanol (ethanol content being about 30 to 95 wt %)), and ginger extract (extract of ginger with water or water-containing ethanol (ethanol content being about 30 to 95 wt %)); and other perfume components. These volatile components may be used either alone as one kind or in combination of two or more kinds. In particular, when a cold sensation imparting agent and a hot sensation imparting agent are used in combination as the volatile component, the sensation of coldness can be imparted while increasing the sensation of hotness that is imparted, so that the sensation of use and the blood flow rate can be improved. Among these volatile components, menthol, camphor, and ginger extract are preferable examples.

The content of the volatile component in the pressure-sensitive adhesive layer 3 is not particularly limited and may be, for example, 0.0001 to 20 wt %, preferably 0.005 to 15 wt %, and more preferably 0.001 to 10 wt %. Here, when the volatile component is an extract, the content refers to a value as converted in terms of dry weight.

Further, in addition to the volatile component, the pressure-sensitive adhesive layer 3 contains a pressure-sensitive adhesive agent as a base in order to provide pressure-sensitive adhesiveness to the adherend.

The pressure-sensitive adhesive agent is a composition that contains a polymer showing a pressure-sensitive adhesiveness (pressure-sensitive adhesive polymer) in the presence of an oil agent, other solvent, or the like where the pressure-sensitive adhesive polymer exhibits pressure-sensitive adhesiveness by being dispersed or dissolved in the oil agent, other solvent, or the like. The type and composition of the pressure-sensitive adhesive polymer contained in the pressure-sensitive adhesive agent are known in the art and, in the present invention, a pressure-sensitive adhesive agent used in the pressure-sensitive adhesive layer 3 of a conventional disposable pocket warmer can be used. Specific examples of the type of the pressure-sensitive adhesive agent include rubber-based pressure-sensitive adhesive agents, acrylic pressure-sensitive adhesive agents, silicone-based pressure-sensitive adhesive agents, and urethane-based pressure-sensitive adhesive agents.

Specific examples of the pressure-sensitive adhesive polymer contained in the rubber-based pressure-sensitive adhesive agent include polystyrene-polybutadiene-polystyrene copolymer, polystyrene-polyisoprene-polystyrene copolymer, polystyrene-polyethylene-polybutylene-polystyrene copolymer, and polystyrene-polyethylene-polypropylene-polystyrene copolymer.

Specific examples of the silicone-based pressure-sensitive adhesive agent include addition-reaction-curing type silicone-based pressure-sensitive adhesive agents and peroxide-curing type silicone-based pressure-sensitive adhesive agents.

Specific examples of the pressure-sensitive adhesive polymer contained in the acrylic pressure-sensitive adhesive agent include (meth)acrylic polymers having an acrylic monomer as a constituent unit, such as methyl acrylate, ethyl acrylate, 2-ethylhexyl acrylate, and butyl acrylate.

Specific examples of the pressure-sensitive adhesive polymer contained in the urethane-based pressure-sensitive adhesive agent include urethane resins obtained by allowing a polyol such as polyether polyol, polyester polyol, polycarbonate polyol, or polycaprolactone polyol to react with polyisocyanate such as diphenylmethane diisocyanate, tolylene diisocyanate, or hexamethylene diisocyanate.

These pressure-sensitive adhesive agents may be used either alone as one kind or as a combination of two or more kinds.

Among these pressure-sensitive adhesive agents, a rubber-based pressure-sensitive adhesive agent is a preferable example.

The content of the pressure-sensitive adhesive agent in the pressure-sensitive adhesive layer 3 may be suitably set in accordance with the pressure-sensitive adhesiveness to the adherend, the type of the pressure-sensitive adhesive agent, and the like, and may be, for example, 60 to 99.9 wt %, preferably 70 to 99 wt %, and more preferably 80 to 98 wt %.

In addition to the aforementioned components, the pressure-sensitive adhesive layer 3 may contain a pharmacological component and a fragrance component in accordance with the needs. Examples of such components include blood circulation promoters such as acidic mucopolysaccharide, matricaria recutita, buckeye, gingko, hamamelis extract, grapefruit extract, rosemary extract, lemon extract, vitamin E, and nicotinic acid derivatives; moisturizing agents such as glycerin, ceramide, collagen, hyaluronic acid, and squalane; fatigue relieving agents such as basil extract and juniper extract; pain relievers such as indometacin, diclofenac, flurbiprofen, ketoprofen, piroxicam, felbinac, methyl salicylate, and glycol salicylate; sliming agents such as tea extract, ginseng extract, caffeine, buckeye, aminophylline, aescin, anthocyanidin, organic iodine compounds, hypericum erectum extract, filipendula extract, horsetail, rosemary, hedera helix, thiomucase, and hyaluronidase; swollenness alleviating agents such as terminalia, ammi visnaga, ammi majus, buckeye, anthocyanin, vitamin P, calendula, konkoritto acid, and silanol; peeling agents such as protease; depilatory agents such as calcium thioglycolate; and autonomic nerve regulating agents such as γ-oryzanol.

These pharmacological components and fragrance components may be used either alone as one kind or in combination of two or more kinds. Also, the content of the pharmacological components and fragrance components in the pressure-sensitive adhesive layer 3 may be suitably set in accordance with the pharmacological effects or fragrance effects that are to be imparted.

The application amount of the pressure-sensitive adhesive layer 3 may be suitably set in accordance with the adhesiveness to the adherend that is to be attached, the area for forming the pressure-sensitive adhesive layer 3, and the like. The application amount of the pressure-sensitive adhesive layer 3 in a region where the pressure-sensitive adhesive layer 3 is formed on the first packaging material 21 may be, for example, 20 to 150 $g/m^2$, preferably 40 to 120 $g/m^2$, and more preferably 60 to 100 $g/m^2$.

The pressure-sensitive adhesive layer 3 may be provided over the whole surface of the first packaging material 21 of the accommodation body 2 or may be partially provided on the first packaging material 21.

A suitable example of the arrangement mode of the pressure-sensitive adhesive layer 3 may be a mode such that the pressure-sensitive adhesive layer 3 is provided on a whole surface or a part of the region of the accommodation section 22 in the first packaging material 21 of the accommodation body 2, and the pressure-sensitive adhesive layer 3 is provided on the whole surface or a part of the region of the peripheral bonding section 24 in the first packaging material 21 of the accommodation body 2. By providing the pressure-sensitive adhesive layer 3 on a whole surface or a part of the region of the accommodation section 22 in the first packaging material 21 in such a manner, the heat generator can be stably fixed onto the adherend at the time of use. Also, by providing the pressure-sensitive adhesive layer 3 on a whole surface or a part of the region of the peripheral bonding section 24 in the first packaging material 21, the adhesion between the release sheet 4 and the pressure-sensitive adhesive layer 3 is improved during storage, and the volatile component can be furthermore stably maintained within the pressure-sensitive adhesive layer 3.

When the pressure-sensitive adhesive layer 3 is provided in the region of the accommodation section 22 in the first packaging material 21, the area ratio of the part where the pressure-sensitive adhesive layer 3 is provided (pressure-sensitive adhesive layer forming part) and the part where the pressure-sensitive adhesive layer 3 is not provided (no pressure-sensitive adhesive layer forming part) in the region may be suitably set in accordance with the adhesiveness to the adherend that is to be attached and the like, and may be typically, for example, 100:0 to 2000, preferably 100:10 to 400, and more preferably 100:25 to 150, as an area ratio of the pressure-sensitive adhesive layer forming part:no pressure-sensitive adhesive layer forming part.

Also, when the pressure-sensitive adhesive layer 3 is provided on the lower surface of the peripheral bonding section 24 in the first packaging material 21, the area ratio of the part where the pressure-sensitive adhesive layer 3 is provided (pressure-sensitive adhesive layer forming part) and the part where the pressure-sensitive adhesive layer 3 is not provided (no pressure-sensitive adhesive layer forming part) on the lower surface of the peripheral bonding section 24 may be suitably set in accordance with the adhesiveness to the adherend that is to be attached and the like, and may be typically, for example, 100:0 to 2000, preferably 100:10 to 400, and more preferably 100:25 to 150, as an area ratio of the pressure-sensitive adhesive layer forming part:no pressure-sensitive adhesive layer forming part.

When the pressure-sensitive adhesive layer 3 is provided partially to the first packaging material 21, the shape of the formed pressure-sensitive adhesive layer 3 is not particularly limited, and may be, for example, a stripe shape, a dot shape, a lattice shape, a net shape, a frame shape surrounding the ends of the first packaging material 21, or the like.

The pressure-sensitive adhesive layer 3 is formed by application onto the first packaging material 21 of the accommodation body 2 using a conventional coating method.

<Release Sheet>

In the heat generator of the present invention, the release sheet 4 including the second gas barrier layer 41 is let to adhere closely over the whole surface of the pressure-sensitive adhesive layer 3 (the side that is attached to the adherend) in a releasable state. By allowing the release sheet 4 including the second gas barrier layer 41 to adhere closely to the pressure-sensitive adhesive layer 3 in this manner, it is possible to prevent the volatile component contained in the pressure-sensitive adhesive layer 3 from being volatilized into the tight sealing bag during storage, and to maintain the volatile component stably within the pressure-sensitive adhesive layer 3.

The oxygen permeability of the release sheet 4 is not particularly limited as long as the release sheet 4 can prevent permeation of the volatile component; however, in view of more effectively preventing the volatile component contained in the pressure-sensitive adhesive layer 3 from being volatilized into the tight sealing bag during storage, the oxygen permeability of the release sheet 4 may be, for example, 1.5 cc/m$^2$·day·atm or less, preferably 0 to 1 cc/m$^2$·day·atm, more preferably 0 to 0.5 cc/m$^2$·day·atm, and still more preferably 0 to 0.1 cc/m$^2$·day·atm.

Also, the water vapor permeability of the release sheet 4 is not particularly limited as long as the release sheet 4 can prevent permeation of the volatile component: however, in view of more effectively preventing the volatile component contained in the pressure-sensitive adhesive layer 3 from being volatilized into the tight sealing bag during storage, the water vapor permeability of the release sheet 4 may be, preferably, 1.5 g/m$^2$·day or less, preferably 0 to 1 g/m$^2$·day, more preferably 0 to 0.5 g/m$^2$·day, and still more preferably 0 to 0.1 g/m$^2$·day.

The material constituting the second gas barrier layer 41 is not particularly limited and may be, for example, a metal foil membrane, a vapor deposition film, a barrier resin layer, or the like.

Specific examples, suitable examples, thickness, forming method, and the like of the metal foil membrane, vapor deposition film, and barrier resin layer used as the second gas barrier layer 41 are similar to those of the first gas barrier layer 211.

In the release sheet 4, the second gas barrier layer 41 may be a single layer made of one constituent material or a multiple layer made of two or more of the same or different materials.

The release sheet 4 including a metal foil membrane, particularly an aluminum foil membrane, as the second gas barrier layer 41 can follow the step difference 2a (height difference) that is formed at the boundary between the peripheral bonding section 24 and the accommodation section 22 of the accommodation body 2, and can enhance the adhesion to the pressure-sensitive adhesive layer 3. This can prevent a gap from being generated between the pressure-sensitive adhesive layer 3 and the release sheet 4 in the region of the peripheral bonding section 24 and can more effectively prevent the volatile component contained in the pressure-sensitive adhesive layer 3 from being volatilized into the tight sealing bag during storage. Here, when the release sheet 4 follows the step difference 2a that is formed at the boundary between the peripheral bonding section 24 and the accommodation section 22 of the accommodation body 2, the release sheet 4 that is in close adhesion to the pressure-sensitive adhesive layer 3 is in a state in which a step difference is formed in correspondence with the step difference 2a.

Also, a substrate layer 42 may be included in the release sheet 4 in order to support or enhance the strength of the second gas barrier layer 41. The substrate layer 42 may be made, for example, of a resin film such as polyethylene terephthalate, polyacrylonitrile, ethylene-vinyl alcohol copolymer, or polypropylene; paper, or the like. Among the substrate layers 42, a resin film is preferable, and a polyethylene terephthalate film is more preferable. Also, these substrate layers 42 may be made of a single layer alone or a multiple layer of two or more layers.

The thickness of the substrate layer 42 is not particularly limited, and may be, for example, 1 to 100 µm, more preferably 3 to 50 µm.

When a laminated body of the second gas barrier layer 41 and the substrate layer 42 is used as the release sheet 4, it is preferable that the second gas barrier layer 41 side is brought into contact with the pressure-sensitive adhesive layer 3 to achieve close adhesion; however, the substrate layer 42 side may be brought into contact with the pressure-sensitive adhesive layer 3 to achieve close adhesion as well.

Also, in the release sheet 4, the surface on the side that is brought into contact with the pressure-sensitive adhesive layer 3 may be subjected to a releasability imparting treatment such as silicone treatment in accordance with the needs.

Also, in a conventional heat generator, an auxiliary cutting line is often carved by providing a penetrating section that penetrates in the thickness direction in the release sheet 4. However, in the heat generator of the present invention, it is preferable that the release sheet 4 does not have a penetrating section that penetrates in the thickness direction. By not providing a penetrating section that penetrates in the thickness direction in the release sheet 4, the volatile component contained in the pressure-sensitive adhesive layer 3 can be more effectively prevented from being volatilized into the tight sealing bag during storage.

Also, in the heat generator of the present invention, the release sheet 4 preferably has a concave-convex shape in the region of the peripheral bonding section 24 of the accommodation body 2 in a state of close adhesion to the pressure-sensitive adhesive layer 3, and the pressure-sensitive adhesive layer 3 preferably has a concave-convex shape that follows the concave-convex shape of the release sheet 4. In this manner, because the pressure-sensitive adhesive layer 3 has a concave-convex shape to follow the concave-convex shape of the release sheet 4 in the region of the peripheral bonding section 24, the adhesion between the pressure-sensitive adhesive layer 3 and the release sheet 4 is made more firm in the region of the peripheral bonding section 24, and the volatile component contained in the pressure-sensitive adhesive layer 3 can be more effectively prevented from being volatilized into the tight sealing bag during storage. Also, when a concave-convex shape is formed in the region of the peripheral bonding section 24 of the accommodation body 2, a concave-convex shape that follows the concave-convex shape of the release sheet 4 may be formed also in the first packaging material 21 and the second packaging material 23 in the region of the peripheral bonding section 24.

When a concave-convex shape is formed on the pressure-sensitive adhesive layer 3 and the release sheet 4 in the region of the peripheral bonding section 24 of the accommodation body 2, the height difference between the concave part and the convex part of the concave-convex shape is not particularly limited, and may be, for example, 1 to 3000 μm, preferably 10 to 1000 μm.

Such a concave-convex shape can be formed by performing an embossing treatment on the region of the peripheral bonding section 24 in a state in which the pressure-sensitive adhesive layer 3 and the release sheet 4 are close adhesion to each other.

<Preferable Modes>

Figure 3:
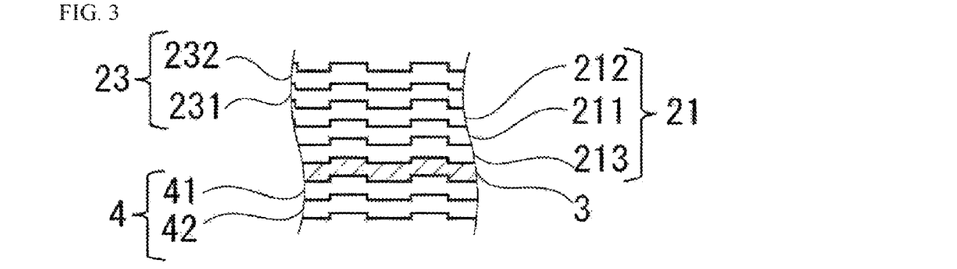
FIG. 3 is an enlarged schematic view of the region E shown in FIG. 1.

FIGS. 1 and 2 each show a schematic view of a cross-sectional structure of one preferable embodiment of the heat generator of the present invention. In the heat generators shown in FIGS. 1 and 2, the accommodation section 22 and the peripheral bonding section 24 are formed by bonding the peripheral parts of the first packaging material 21 and the second packaging material 23, and further, the accommodation body 2 having a step difference 2a at the boundary between the accommodation section 22 and the peripheral bonding section 24 is formed. A heat-generating composition that generates heat by being brought into contact with oxygen is accommodated as a heat-generating section 1 in the accommodation body 2. In the heat generator shown in FIG. 1, the first packaging material 21 of the accommodation body 2 is configured from a lamination sheet in which a welded resin layer 212, a first gas barrier layer 211 made of a metal foil membrane, and a fiber substrate 213 are laminated in this order in a direction from the accommodation section 22 side towards the attachment surface. In the heat generator shown in FIG. 2, the first packaging material 21 of the accommodation body 2 is configured from a lamination sheet in which a welded resin layer 212, a first resin layer 214, a first gas barrier layer 211 made of a vapor deposition film, and a fiber substrate 213 are laminated in this order in a direction from the accommodation section 22 side towards the attachment surface. Also, in the heat generators shown in FIGS. 1 and 2, the second packaging material 23 of the accommodation body 2 is formed of a lamination sheet in which a gas-permeable resin layer 231 and a fiber substrate 232 are laminated in this order in a direction from the accommodation section 22 side towards the outside. In the heat generators shown in FIGS. 1 and 2, a pressure-sensitive adhesive layer 3 is laminated on the first packaging material 21 of the accommodation body 2, and the release sheet 4 is in close adhesion to the pressure-sensitive adhesive layer 3 by following the step difference 2a. Also, in the heat generators shown in FIGS. 1 and 2, the release sheet 4 is formed of a lamination sheet in which the second gas barrier layer 41 and the substrate layer 42 are laminated in this order in a direction from the pressure-sensitive adhesive layer 3 side. Also, FIG. 3 shows an enlarged schematic view of the region E shown in FIG. 1. In FIG. 3, the release sheet 4 is formed to have a concave-convex shape in the peripheral bonding section 24, and each of the layers constituting the pressure-sensitive adhesive layer 3, the first packaging material 21, and the second packaging material 23 is formed to have a concave-convex shape so as to follow the concave-convex shape of the release sheet 4.

<Mode of Use • Packaging Mode>

The heat generator of the present invention is used as a warming tool or a curing tool of a human body by attaching the pressure-sensitive adhesive layer 3 to the adherend such as a skin or clothing. In particular, since the heat generator of the present invention can achieve an excellent warming function, the heat generator is particularly suitably used as a curing tool for blood circulation promotion, pain alleviation, stiff shoulder alleviation, or the like.

The adherend serving as an object of applying the heat generator of the present invention may be one that demands warming, and may be, for example, a skin, a clothing, or the like. Among the adherends, a skin is suitable. When the heat generator of the present invention is used by being attached to a skin, the skin site serving as an object of attachment is not particularly limited and may be, for example, an eye, a face, a neck, a shoulder, a waist, a back, a belly, a buttock, an arm, a leg, a foot bottom, or the like. Also, when the heat generator of the present invention is used by being attached to a clothing, the heat generator of the present invention may be attached to a site of the clothing corresponding to the site of the human body to which it is wished to impart warming. Also, the type of the clothing serving as an object of applying the heat generator of the present invention is not particularly limited, however, the type of the clothing is preferably an underwear in view of efficiently imparting warming to the human body.

When the heat-generating section 1 is a heat-generating composition that generates heat by being brought into contact with oxygen, the heat generator of the present invention is accommodated in a tight sealing bag having an oxygen barrier property, so as to provide the heat-generating composition in a state that is not contact with air. By opening the tight sealing bag at the time of use, the heat-generating composition is brought into contact with air, and the heat generation starts.

EXAMPLES

The present invention will be more specifically described by showing Examples; however, the present invention is not limited to these.

Test Example 1

1. Production of Heat Generator

First packaging materials A to D (rectangles with a longitudinal side being 13 cm and a lateral side being 9.5 cm) each made of a non-gas-permeable lamination sheet having a layer configuration shown in Table 1 were prepared. Also, for each of the first packaging materials, the oxygen permeability was measured under conditions with a temperature of 20° C. and a humidity of 90% RH in accordance with the differential pressure method defined in JIS K 7126-1:2006. Further, for each of the first packaging materials, the water vapor permeability was measured under conditions with a temperature of 40° C. and a humidity of 90% RH in accordance with the cup method defined in JIS Z0208:1976.

TABLE 1

| | Layer structure | Oxygen permeability (cc/m² · day) | Water vapor permeability (g/m² · day) |
|---|---|---|---|
| First packaging material A | Lamination sheet in which a polyethylene film (having a thickness of 30 μm), an aluminum foil membrane (having a thickness of 9 μm), and a nonwoven cloth (made of polyethylene terephthalate, weight per unit area of 30 g/m²) are laminated in this order. Bonding between the polyethylene film and the aluminum foil membrane and between the aluminum foil membrane and the nonwoven cloth was carried out by dry lamination | 0.1 | 0.1 |
| First packaging material B | Lamination sheet in which a polyethylene film (having a thickness of 30 μm), a polyethylene terephthalate layer (having a thickness of 12 μm), a vapor deposition film made of aluminum oxide (having a thickness of 500 Å), and a nonwoven cloth (made of polyethylene terephthalate, weight per unit area of 30 g/m²) are laminated in this order. Bonding between the polyethylene film and the polyethylene terephthalate layer and between the vapor deposition film and the nonwoven cloth was carried out by dry lamination. The vapor deposition film was formed by vapor deposition of aluminum oxide onto the polyethylene terephthalate layer. | 1.5 | 1.5 |
| First packaging material C | Lamination sheet in which a polyethylene film (having a thickness of 30 μm), a polyethylene terephthalate layer (having a thickness of 12 μm), a vapor deposition film made of silica (having a thickness of 500 Å), and a nonwoven cloth (made of polyethylene terephthalate, weight per unit area of 30 g/m²) are laminated in this order. Bonding between the polyethylene film and the polyethylene terephthalate layer and between the vapor deposition film and the nonwoven cloth was carried out by dry lamination. The vapor deposition film was formed by vapor deposition of silica onto the polyethylene terephthalate layer. | 0.5 | 0.5 |
| First packaging material D | Lamination sheet in which a polyethylene film (having a thickness of 30 μm), a polyethylene terephthalate layer (having a thickness of 12 μm), and a nonwoven cloth (made of polyethylene terephthalate, weight per unit area of 30 g/m²) are laminated in this order. Bonding between the polyethylene film and the polyethylene terephthalate layer and between the polyethylene terephthalate layer and the nonwoven cloth was carried out by dry lamination. | 25.2 | 15.7 |

A pressure-sensitive adhesive layer forming composition 1 containing the following components that were mixed by heating at 140° C. was applied onto the whole surface of the nonwoven cloth of the first packaging material so as to attain an application amount of 100 g/m², followed by cooling to form a pressure-sensitive adhesive layer on the first packaging material.

<Pressure-Sensitive Adhesive Layer Forming Composition 1>

Menthol (trade name: "HAKKANO", manufactured by Nagaoka & Co., Ltd.): 5 wt %
Rubber-based pressure-sensitive adhesive agent: 95 wt %
Total: 100 wt %

Release sheets A to C (rectangles with a longitudinal side being 13 cm and a lateral side being 9.5 cm) each having a layer configuration shown in Table 2 were prepared. The oxygen permeability and the water vapor permeability of the release sheets were measured by methods similar to those described above. Subsequently, each release sheet was bonded to the pressure-sensitive adhesive layer on the first packaging material. During this, the release sheets A to C were placed so that the aluminum foil membrane side of the release sheet A, the vapor deposition film side of the release sheet B, and the surface of the release sheet C subjected to a silicone treatment would be in surface contact with the respective pressure-sensitive adhesive layers.

TABLE 2

| | Layer structure | Oxygen permeability (cc/m² · day) | Water vapor permeability (g/m² · day) |
|---|---|---|---|
| Release sheet A | Lamination sheet in which an aluminum foil membrane (having a thickness of 9 μm) and a polyethylene terephthalate layer (having a thickness of 12 μm) are laminated in this order. Bonding between the aluminum foil membrane and the polyethylene terephthalate layer was carried out by dry lamination | 0.1 | 0.1 |
| Release sheet B | Lamination sheet in which a vapor deposition film made of aluminum oxide (having a thickness of 500 Å) and a polyethylene terephthalate layer (having a thickness of 12 μm) | 1.5 | 1.5 |

TABLE 2-continued

| | Layer structure | Oxygen permeability (cc/m² · day) | Water vapor permeability (g/m² · day) |
|---|---|---|---|
| | are laminated in this order. The vapor deposition film was formed by vapor deposition of aluminum oxide onto the polyethylene terephthalate layer. | | |
| Release sheet C | Polyethylene terephthalate film subjected to a silicone treatment (having a thickness of 12 μm). | 25.2 | 15.7 |

Also, a second packaging material (rectangle with a longitudinal side being 13 cm and a lateral side being 9.5 cm) made of a gas-permeable lamination sheet in which a polyethylene film (having a thickness of 70 μm) provided with pores and a nonwoven cloth (made of polyethylene terephthalate, weight per unit area of 30 g/m²) had been bonded by dry lamination was separately prepared.

Subsequently, 22 g of iron powder, 6 g of activated carbon, and 10 g of a mixture of water-soluble salt, water retention agent, and water (mixture of sodium chloride, water-absorbing resin, vermiculite, water, and the like; containing 8.5 g of water) were mixed to prepare a heat-generating composition. The peripheral parts of the first packaging material and the second packaging material were thermally welded with each other in a state in which 38 g of the obtained heat-generating composition had been interposed between the polyethylene film side of the first packaging material and the polyethylene film side of the second packaging material, and the heat-generating composition was accommodated in the formed accommodation section (with a longitudinal side being 12 cm and a lateral side being 8.5 cm). Subsequently, the peripheral bonding section where the first packaging material and the second packaging material had been welded was subjected to an embossing treatment using an embossing template with an undulation depth of 200 μm from the release sheet side to form a concave-convex shape from the surface of the release sheet down to the depth reaching the pressure-sensitive adhesive layer, thereby to form a heat generator. The produced heat generator was quickly accommodated into a non-gas-permeable sealing bag and tightly sealed. Here, in the produced heat generator, combinations of the first packaging material and the second packaging material shown in Table 3 were adopted.

In the obtained heat generators of Examples 1, 3, and 4, it was found out that the release sheet sufficiently followed the step difference generated at the boundary between the peripheral bonding section and the accommodation section of the accommodation body, and the adhesion between the pressure-sensitive adhesive layer and the release sheet had been enhanced in the peripheral bonding section region.

2. Evaluation of Retained Amount of Menthol in Pressure-Sensitive Adhesive Layer by Storage The heat generator accommodated in the tight sealing bag was stored at 50° C. for two months. The pressure-sensitive adhesive layer of the heat generators immediately after production and after storage for two months was peeled off, and this was added into chloroform and subjected to a supersonic wave treatment for 30 minutes to extract menthol. Subsequently, the amount of extracted menthol was measured by gas chromatography so as to determine the amount of menthol in the pressure-sensitive adhesive layer. Also, the retention rate of menthol in the pressure-sensitive adhesive layer was calculated in accordance with the following calculation formula.

Retention rate (%) of menthol in pressure-sensitive adhesive layer={(amount of menthol in pressure-sensitive adhesive layer after storage for two months)/(amount of menthol in pressure-sensitive adhesive layer immediately after production)}×100  [Numerical formula 1]

The obtained results are shown in Table 3. The amount of menthol in the pressure-sensitive adhesive layer greatly decreased after storage for two months in the case in which the gas barrier layer had not been provided in the release sheet even though a gas barrier layer made of a metal foil membrane or a vapor deposition film had been provided in the first packaging material (Comparative Examples 1 and 2). Also, the amount of menthol in the pressure-sensitive adhesive layer greatly decreased after storage for two months even when a gas barrier layer made of a vapor deposition film had been provided in the release sheet without providing a gas barrier layer in the first packaging material (Comparative Example 3). In contrast, menthol was stably maintained in the pressure-sensitive adhesive layer even after storage for two months when a gas barrier layer made of a metal foil membrane or a vapor deposition film had been provided in both of the first packaging material and the release sheet (Examples 1 to 5). Also, the retention rate of menthol in the pressure-sensitive adhesive layer after storage was outstandingly enhanced when the oxygen permeability of the gas barrier layer provided in the first packaging material was 1.5 cc/m²·day or less, particularly when the oxygen permeability was 0.1 cc/m²·day or less. Also, in a similar manner, the retention rate of menthol in the pressure-sensitive adhesive layer after storage was outstandingly enhanced when the oxygen permeability of the gas barrier layer provided in the releases sheet was 1.5 cc/m²·day or less, particularly when the oxygen permeability was 0.1 cc/m²·day or less.

TABLE 3

| | First packaging material | | | | Release sheet | |
|---|---|---|---|---|---|---|
| | | Gas barrier layer | Oxygen permeability | Water vapor permeability | | Gas barrier layer |
| | Type | put to use | (cc/m² · day) | (g/m² · day) | Type | put to use |
| Example 1 | A | Metal foil membrane | 0.1 | 0.1 | A | Metal foil membrane |
| Example 2 | A | Metal foil membrane | 0.1 | 0.1 | B | Vapor deposition film |
| Example 3 | B | Vapor deposition film | 1.5 | 1.5 | A | Metal foil membrane |
| Example 4 | C | Vapor deposition film | 0.5 | 0.5 | A | Metal foil membrane |
| Example 5 | B | Vapor deposition film | 1.5 | 1.5 | B | Vapor deposition film |
| Comparative Example 1 | B | Vapor deposition film | 1.5 | 1.5 | C | None |

TABLE 3-continued

| | | | | | |
|---|---|---|---|---|---|
| Comparative Example 2 | A | Metal foil membrane | 0.1 | 0.1 | C None |
| Comparative Example 3 | D | None | 25.2 | 15.7 | B Vapor deposition film |

| | Release sheet | | Amount of menthol in pressure-sensitive adhesive layer immediately after production (wt %) | Amount of menthol in pressure-sensitive adhesive layer after storage for two months (wt %) | Retention rate of menthol in pressure-sensitive adhesive layer (%) |
|---|---|---|---|---|---|
| | Oxygen permeability (cc/m² · day) | Water vapor permeability (g/m² · day) | | | |
| Example 1 | 0.1 | 0.1 | 3.9 | 3.6 | 92.3 |
| Example 2 | 1.5 | 1.5 | 3.9 | 2.8 | 71.8 |
| Example 3 | 0.1 | 0.1 | 3.9 | 3.2 | 82.1 |
| Example 4 | 0.1 | 0.1 | 3.9 | 3.1 | 79.5 |
| Example 5 | 1.5 | 1.5 | 3.9 | 2.6 | 66.7 |
| Comparative Example 1 | 25.2 | 15.7 | 3.9 | 0.7 | 17.9 |
| Comparative Example 2 | 25.2 | 15.7 | 3.9 | 0.9 | 23.1 |
| Comparative Example 3 | 1.5 | 1.5 | 3.9 | 0.1 | 2.6 |

3. Evaluation of Heat Generation Characteristics of Heat Generator after Storage The heat generators immediately after production (Example 1 and Comparative Example 1) were each put into a tight sealing bag and stored at 50° C. for two months. Thereafter, the heat generation characteristics were evaluated. Specifically, 10 pieces of heat generators were each taken out from the tight sealing bag, and the heat generation temperature was measured with lapse of time from the time point at which the heat generators were taken out from the tight sealing bag in accordance with the method defined in JIS S 4100:2007.

Figure 4:
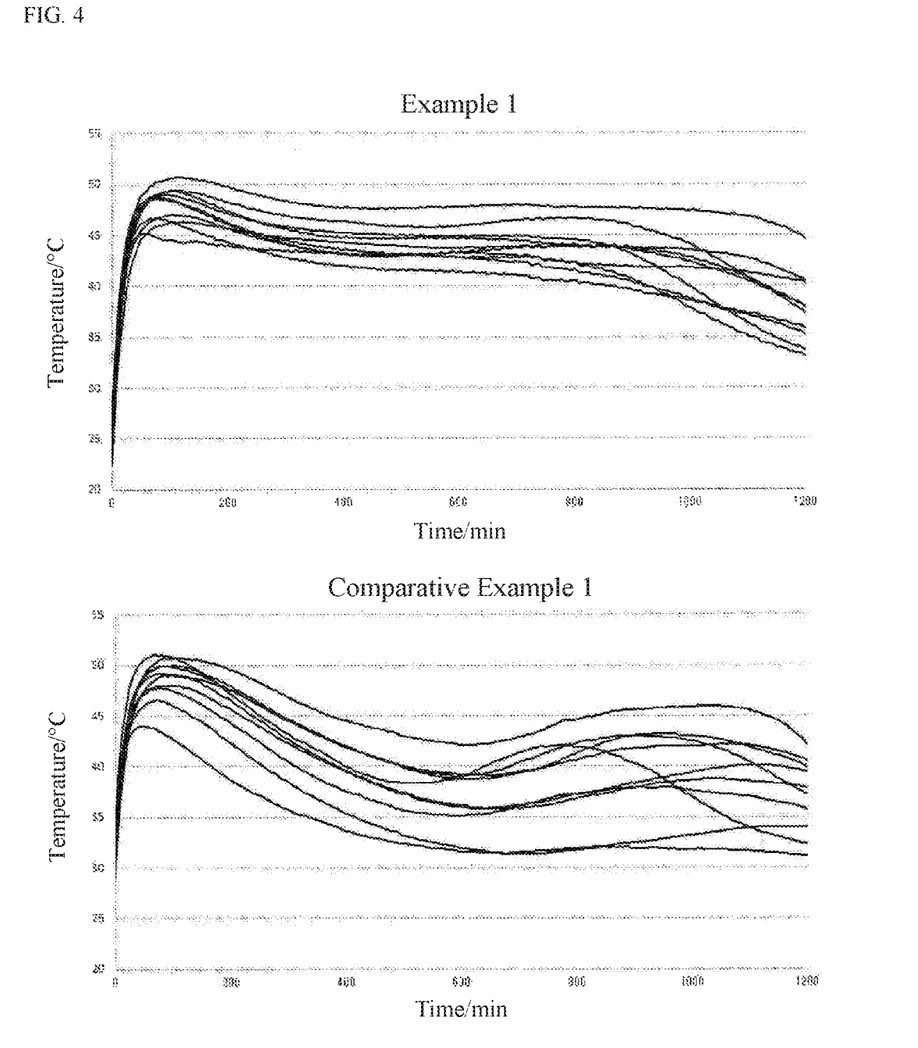
FIG. 4 is a graph showing results of evaluating the heat generation characteristics after the heat generators of Example 1 and Comparative Example 1 (each with 10 pieces) were stored at 50° C. for two months.

The obtained results are shown in FIG. 4. As a result of this, it was found out that, in the heat generators of Comparative Example 1, the heat generation temperature decreased during the period from the time of 120 minutes to the time of 600 minutes after the heat generator was taken out from the tight sealing bag, and further, variation in the heat generation temperature among the 10 pieces of heat generators was large. Also, in some of the heat generators of Comparative Example 1, the temperature rose after the temperature once lowered, thereby failing to show a stable heat generation behavior. In contrast, in the heat generators of Example 1, heat was generated stably at a temperature of 40° C. or higher during the period from the time of 20 minutes to the time of 780 minutes after the heat generator was taken out from the tight sealing bag, and also variation in the heat generation temperature among the 10 pieces of heat generators was small. In the heat generators of Example 1, it seems that menthol was stably maintained in the pressure-sensitive adhesive layer during storage, and menthol was prevented from adhering to the heat-generating composition. As a result of this, a stable heat generation temperature was realized, and the heat generation temperature was uniform among the 10 pieces of heat generators.

Test Example 2

1. Production of Heat Generator

Example 6

A heat generator was produced under the same conditions as in the aforementioned Example 1 except that the pressure-sensitive adhesive layer forming composition 2 containing the following components was used.

<Pressure-Sensitive Adhesive Layer Forming Composition 2>

Menthol (trade name: "HAKKANO", manufactured by Nagaoka & Co., Ltd.): 5 wt %

Camphor (trade name: "dl-camphor [SP]", manufactured by Nagaoka & Co., Ltd.): 1.5 wt %

Ginger extract (trade name: "Ginger Extract Liquid", manufactured by Alps Pharmaceutical Industry Co., Ltd.) (liquid form) (corresponding to about 0.12 wt % as converted in terms of dry raw material): 3 wt %

Rubber-based pressure-sensitive adhesive agent: 90.5 wt %

Total: 100 wt %

Comparative Example 4

A heat generator was produced under the same conditions as in the aforementioned Example 6 except that the first packaging material D and the release sheet C were used.

2. Evaluation of Sensation of Hotness and Sensation of Coldness of Heat Generator after Storage The heat generators immediately after production (Example 6 and Comparative Example 4) were each put into a tight sealing bag and stored at 50° C. for two months. Thereafter, the sensation of hotness and the sensation of coldness were evaluated by 10 subject persons being tested. Specifically, after the subject person being tested maintained for 10 minutes a posture in which the forearm was placed on a desk having the same height as the heart in a sitting position, the heat generator taken out from the tight sealing bag was directly attached to the forearm on the desk. Thereafter, the sensation of hotness and the sensation of coldness that are exhibited every 5 minutes during the time of 50 minutes were scored in accordance with the following determination standard, and an average value thereof was calculated.

(Determination Standard of Sensation of Hotness and Sensation of Coldness)

5: Extremely strongly perceived

4: Strongly perceived

3: Perceived

2: A little weakly perceived
1: Not perceived at all

Figure 5:
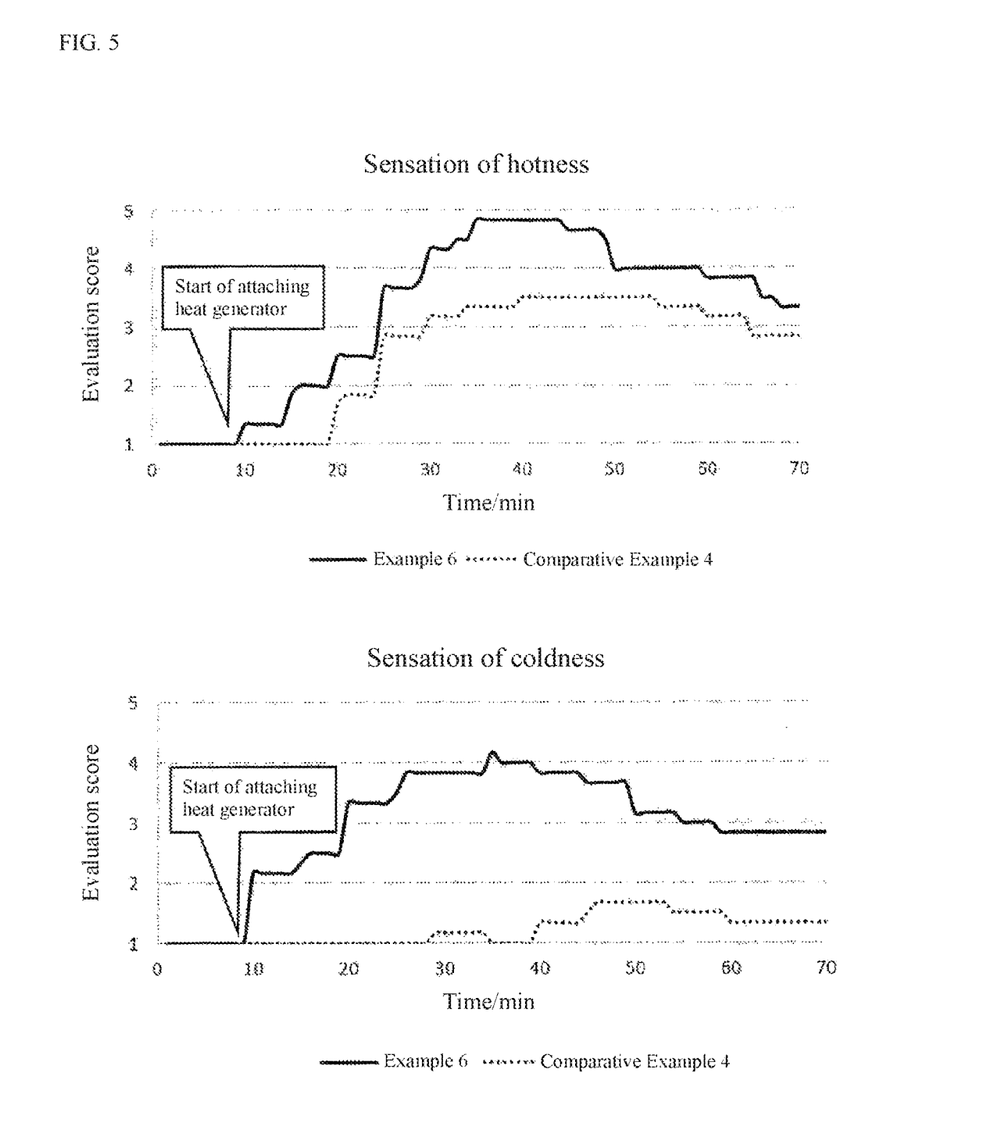
FIG. 5 is a graph showing results of evaluating over time the sensation of hotness and the sensation of coldness that were perceived after the heat generators of Example 6 and Comparative Example 4 (each with 10 pieces) were stored at 50° C. for two months.

The obtained results are shown in FIG. 5. As a result of this, it has been made clear that, in the heat generator of Example 6, the sensation of hotness perceived from the time of the start of use was perceived early, and further, the sensation of hotness was strongly perceived as compared with the heat generator of Comparative Example 4. In the heat generator of Example 6, the first packaging material has a metal foil membrane, and it seems that an early onset of the sensation of hotness and a stronger sensation of hotness were realized by improvement in the thermal conductivity and generation of radiation heat brought about by the metal foil membrane. Also, in the heat generator of Example 6, the sensation of coldness was sufficiently perceived as compared with the heat generator of Comparative Example 4.

DESCRIPTION OF REFERENCE SIGNS

1: Heat-generating section
2: Accommodation body
2a: Step difference (height difference)
21: First packaging material
211: First gas barrier layer
212: Welded resin layer
213: Fiber substrate
214: First resin layer
22: Accommodation section
23: Second packaging material
231: Gas-permeable resin layer
232: Fiber substrate
24: Peripheral bonding section
3: Pressure-sensitive adhesive layer
4: Release sheet
41: Second gas barrier layer
42: Substrate layer

The invention claimed is:

1. A heat generator that is used by being attached to an adherend, the heat generator comprising:
   a heat-generating section for generating heat that is transmitted to the adherend;
   an accommodation body for accommodating the heat-generating section, the accommodation body having an attachment surface that is attached to the adherend;
   a pressure-sensitive adhesive layer provided to an attachment surface side of the accommodation body; and
   a release sheet provided to an attachment surface side of the pressure-sensitive adhesive layer and being releasable from the pressure-sensitive adhesive layer, wherein
   the pressure-sensitive adhesive layer contains a volatile component,
   a first packaging material disposed on the attachment surface side of the accommodation body includes a first gas barrier layer, and
   the release sheet includes a second gas barrier layer, wherein prior to use, the second gas barrier layer is manufactured as part of the release sheet.

2. The heat generator according to claim 1, wherein the first packaging material has an oxygen permeability of 1.5 $cc/m^2 \cdot day \cdot atm$ or less.

3. The heat generator according to claim 1, wherein the release sheet has an oxygen permeability of 1.5 $cc/m^2 \cdot day \cdot atm$ or less.

4. The heat generator according to claim 1, wherein the first packaging material has a water vapor permeability of 1.5 $g/m^2 \cdot day \cdot atm$ or less.

5. The heat generator according to claim 1, wherein the release sheet has a water vapor permeability of 1.5 $g/m^2 \cdot day \cdot atm$ or less.

6. The heat generator according to claim 1, wherein
   the accommodation body is composed of the first packaging material and a second packaging material that is disposed on a surface opposite to the attachment surface,
   the accommodation body includes a peripheral bonding section where peripheral parts of the first packaging material and the second packaging material are bonded, and an accommodation section that forms a space for accommodating the heat-generating section, and
   the pressure-sensitive adhesive layer is provided at least in a region where the peripheral bonding section of the first packaging material is formed.

7. The heat generator according to claim 1, wherein the volatile component is at least one kind selected from the group consisting of menthol, camphor, thymol, spilanthol, mint oil, peppermint oil, methyl salicylate, capsaicin, vanillyl nonylic acid amide, sage, caffeine, tocopherol nicotinate, benzyl nicotinate, vanillyl butyl ether, vanillyl ethyl ether, gingerol, vanillyl propyl ether, vanillyl pentyl ether, vanillyl hexyl ether, vanillyl butyl ether acetate, hot pepper extract, and ginger extract.

8. The heat generator according to claim 1, wherein the release sheet does not have a penetrating section that penetrates in a thickness direction.

* * * * *